(12) United States Patent
Evans et al.

(10) Patent No.: US 6,756,491 B2
(45) Date of Patent: *Jun. 29, 2004

(54) STEROID-ACTIVATED NUCLEAR RECEPTORS AND USES THEREFOR

(75) Inventors: Ronald M. Evans, La Jolla, CA (US); Bruce Blumberg, San Diego, CA (US)

(73) Assignee: The Salk Institute for Biological Studies, La Jolla, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/005,286

(22) Filed: Jan. 9, 1998

(65) Prior Publication Data

US 2003/0064430 A1 Apr. 3, 2003

(51) Int. Cl.[7] .......................... C12Q 1/70; G01N 33/53
(52) U.S. Cl. ............... 536/23.1; 536/23.5; 536/24.31; 435/69.1
(58) Field of Search ............................. 536/23.1, 23.5, 536/24.31; 435/69.1

(56) References Cited

U.S. PATENT DOCUMENTS 5,639,616 A * 6/1997 Liao et al. .................. 435/7.1
5,726,041 A * 3/1998 Chrespi et al. ............ 435/69.1

FOREIGN PATENT DOCUMENTS

| WO | 99/19354 | 4/1999 |
| WO | WO 99/19354 | 4/1999 |
| WO | WO 99/48915 | 9/1999 |
| WO | 99/489915 | 9/1999 |
| WO | 99/61622 | 12/1999 |
| WO | WO 99/61622 | 12/1999 |

OTHER PUBLICATIONS

Adlercreutz and Mazur, "Phyto–oestrogens and Western Diseases" *Ann. Med.* 29:95–120 (1997).*
Altschul, et al., "Basic Local Alignment Search Tool" *J. Mol. Biol.* 215:403–140 (1990).*
Baes, et al., "A New Orphan Member of the Nuclear Hormone Receptor Superfamily That Interacts with a Subset of Retinoic Acid Response Elements" *Molecular and Cellular Biology* 14 (3):1544–1552 (1994).*
Bahouth, et al., "Immunological approaches for probing receptor structure and function" *TIPS* (12):338–343 (1991).*

(List continued on next page.)

*Primary Examiner*—Lori A. Clow
*Assistant Examiner*—Mary K Zeman
(74) *Attorney, Agent, or Firm*—Stephen E. Reiter; Foley & Lardner

(57) ABSTRACT

In accordance with the present invention, there is provided an example of a novel class of nuclear receptor(s), termed the steroid X receptor (SXR). SXR is expressed almost exclusively in the liver, the primary site of xenobiotic and steroid catabolism. Unlike classical steroid receptors, SXR heterodimerizes with RXR and binds to directly repeated sequences related to the half-site, AGTTCA. SXR can activate transcription through response elements found in some steroid inducible P450 genes in response to a wide variety of natural and synthetic steroid hormones, including antagonists such as PCN—ideal properties for a "steroid sensing receptor" which mediates the physiological effect(s) of hormones. SXR represents the first new class of steroid receptors described since the identification of the mineralocorticoid receptor ten years ago. Also provided according to the invention are nucleic acid sequences encoding the above-identified receptors, as well as constructs and cells containing same, and probes derived therefrom. Furthermore, it has also been discovered that a wide variety of substrates modulate the transcription activating effects of invention receptors.

31 Claims, 5 Drawing Sheets

OTHER PUBLICATIONS

Beato, et al., "Steroid Hormone Receptors: Many Actors in Search of Plot" *Cell*,83:851–857 (1995).*

Blumberg, et al., "Novel retinoic acid receptor ligands in Xenopus embryos" *Proc. Natl. Acad. Sci. USA* 93:4873–4878 (1996).*

Burger, et al., "Paradoxical transcriptional activation of rat liver cytochrome P–450 3A1 by dexamethasone and the antiglucocorticoid pregnenolone 16α–carbonitrile: Analysis by transient transfection into primary monolayer cultures of adult rat hepatocytes" *Proc. Natl. Acad. Sci. USA* 89:2145–2149 (1992).*

*Current Protocols in Molecular Biology* (Ausubel et al., eds.) John Wiley and Sons, New York (1989).*

Denison and Whitlock, Jr., "Xenobiotic–inducible Transcription of Cytochrome P450 Genes" *The Journal of Biological Chemisry* 270 (31):18175–18178 (1995).*

Devereaux, et al., "A comprehensive set of sequence analysis programs for the VAX" *Nucleic Acids Research* 12 (1):387–395 (1984).*

Elshourbagy and Guzelian, "Separation, Purification, and Characterization of a Novel Form of Hepatic Cytochrome P–450 from Rats Treated with Pregnenolone–16α–carbonitrile" *The Journal of Biological Chemistry* 255 (4):1279–1285 (1980).*

Enmark and Gustafsson, "Orphan Nuclear Receptors—The First Eight Years" *Molecular Endocrinology* 10 (11):1293–1307 (1996).*

Evans, R. M., "The Steroid and Thyroid Hormone Receptor Superfamily" *Science* 240:889–895 (1988).*

Fernandez–Salguero and Gonzalez, "The CYP2A gene subfamily: species differences, regulation, catalytic activities and role in chemical carcinogenesis" *Pharmacogenetics* 5:S123–S128 (1995).*

Forman, et al., "Hypolipidemic drugs, polyunsaturated fatty acids, and eicosanoids are ligands for peroxisome proliferator–activated receptors α and δ" *Proc. Natl. Acad. Sci. USA* 94:4312–4317 (1997).*

Forman, et al., "Unique in Response Pathways Are Established by Allosteric Interactions among Nuclear Hormone Receptors" *Cell* 81:541–550 (1995).*

Gonzalez, et al., "Complete cDNA and Protein Sequence of a Pregnenolone 16α–Carbonitrile–induced Cytochrome P–450" *The Journal of Biological Chemistry* 260 (12):7435–7441 (1985).*

Gonzalez, et al., "Pregnenolone 16α–Carbonitrile–Inducible P–450 Gene Family: Gene Conversion and Differential Regulation" *Molecular and Cellular Biology* 6 (8):2969–2976 (1986).*

Gottlicher, et al., "Fatty acids activate a chimera of the clofibric acid–activated receptor and the glucocorticoid receptor" *Proc. Natl. Acad. Sci. USA* 89:4653–4657 (1992).*

Hankinson, O., "The Aryl Hydrocarbon Receptor Complex" *Ann. Rev. Pharmacol. Toxicol.* 35:307–340 (1995).*

Hardwick, et al., "Cloning of DNA Complementary to Cytochrome P–450 Induced by Pregnenolone–16α–carbonitrile" *The Journal of Biological Chemistry* 258 (16):10182–10186 (1983).*

Henikoff and Henikoff, "Amino acid substitution matrices from protein blocks" *Proc. Natl. Acad. Sci. USA* 89:10915–10919 (1992).*

Heuman, et al., "Immunochemical Evidence for Induction of a Common Form of Hepatic Cytochrome P–450 in Rats Treated with Pregnenolone–16α–carbonitrile or other Steroidal or Non–Steroidal Agents" *Molecular Pharmacology* 21:753–760 (1982).*

Hollenberg, et al., "Primary structure and expression of a functional human glucocorticoid receptor cDNA" *Nature* 318 (6047):635–641 (1985).*

Jonat, et al., "Antitumor Promotion and Antiinflammation: Down–Modulation of AP–1 (Fos/Jun) Activity by Glucocorticoid Hormone" *Cell* 62:1189–1204 (1990).*

Juchau, M.R., "Substrate Specificities and Functions of the P450 Cytochromes" *Life Sciences* 47:2385–2394 (1990).*

Ladias and Karathanasis, "Regulation of the Apolipoprotein AI Gene by ARP–1, a Novel Member of the Steroid Receptor Superfamily" *Science* 251:561–565 (1991).*

Mangelsdorf and Evans, "The RXR Heterodimers and Orphan Receptors" *Cell* 83:841–850 (1995).*

Mangelsdorf, et al., "The Nuclear Receptor Superfamily: The Second Decade" *Cell* 83:835–839 (1995).*

Miyata, et al., "Transcriptional Elements Directing a Liver–Specific Expression of P450/6βA (CYP3A2) Gene–Encoding Testosterone 6β–Hydroxylase" *Archives of Biochemistry and Biophysics* 318 (1):71–79 (1995).*

Nebert and Gonzalez, P450 Genes:Structure, Evolution, and Regulation *Ann. Rev. Biochem.* 56:945–993 (1987).*

Needleman and Wunsch, "A General Method Applicable to the Search for Similarities in the Amino Acid Sequence of Two Proteins" *J. Mol. Biol.* 48:443–453 (1970).*

O'Malley and Conneely, "Orphan Receptors: In Search of Unifying Hypothesis for Activation" *Molecular Endocrinology* 6 (9):1359–1361 (1992).*

Ogura and Evans, A retinoic acid–triggered cascade of HOXB1 gene activation *Proc. Natl. Acad. Sci. USA* 92:387–391 (1995).*

Perlmann et al., "Determination for selective RAR and TR recognition of direct repeat HREs" *Genes Dev.* 7:1411–1422 (1993).*

Quattrochi, et al., "A Novel cis–Acting Element in a Liver Cytochrome P450 3A Gene Confers Synergistic Induction by Glucocorticoids plus Antiglucocorticoids" *The Journal of Biological Chemistry* 270 (48):28917–28923 (1995).*

Russell and Wilson, "Steroid 5α–Reductase: Two Genes/Two Enzymes" *Ann. Rev. Biochem.* 63:25–61 (1994).*

Scheutz and Guzelian, "Induction of Cytochrome P–450 by Glucocorticoids in Rat Liver I. Evidence That Glucocorticoids Regulate Induction of Cytochrome p–450 By a Nonclassical Receptor Mechanism" *The Journal of Biological Chemistry* 259 (3):2007–2012 (1984).*

Scheutz, et al., "Induction of Cytochrome P–450 by Glucocorticoids in Rat Liver I. Evidence That Glucocorticoids and Pregnenolone 16α–Carbonitrile Regulate De Novo Synthesis of a Common Form of Cytochrome P–450 in Cultures of Adult Rat Hepatocytes and in the Liver in vivo" *The Journal of Biological Chemistry* 259 (3):1999–2006 (1984).*

Schuele, et al., "Functional Antagonism between Oncoprotein c–Jun and the Glucocorticoid Receptor" *Cell* 62:1217–1226 (1990).*

Selye, H., "Hormones and Resistance" *Journal of Pharmaceutical Sciences* 60 (1):1–28 (1971).*

Smith, et al., "A novel nuclear receptor superfamily member in Xenopus that associates with RXR, and shares extensive sequence similarity to the mammalian vitamin D3 receptor" *Nucleic Acids Research* 22 (1):66–71 (1994).*

Staden, R., "The current status and portabiilty of our sequence handling software" *Nucleic Acids Research* 14 (1):217–231 (1986).*

Sucov, et al., "Characterization of an autoregulated response element in the mouse retinoic acid receptor type β gene" *Proc. Natl. Acad. Sci. USA* 87:5392–5396 (1990).*

Umesono et al., "Direct Repeats as Selective Response Elements for the Thyroid Hormone, Retinoic Acid, and Vitamin $D_3$ Receptors" *Cell* 65:1255–1266 (1991).*

Willy, et al., "LXR, a nuclear receptor that defines a distinct retinoid response pathway" *Genes & Development* 9:1033–1045 (1995).*

Yang–Yen, et al., "Transcriptional Interference between c–Jun and the Glucocorticoid Receptor: Mutual Inhibition of DNA Binding Due to Direct Protein–Protein Interaction" *Cell* 62:1205–1215 (1990).*

AA 107961, Genbank, Nov. 4, 1996.*

AA277370, Genbank, Apr. 1, 1997.*

AA679591, Genbank, Dec. 19, 1997.*

* cited by examiner

SEQUENCE LISTING

<160> NUMBER OF SEQ ID NOS: 21

<210> SEQ ID NO 1
<211> LENGTH: 2068
<212> TYPE: DNA
<213> ORGANISM: Homo sapiens
<220> FEATURE:
<221> NAME/KEY: CDS
<222> LOCATION: (493)...(1884)
<223> OTHER INFORMATION: N is selected from A, C, T/U or G

<400> SEQUENCE: 1

```
ggcacgagga gatctaggtt caaattaatg ttgcccctag tggtaaagga cagagaccct      60
cagactgatg aaatgcgctc agaattactt agacaaagcg gatatttgcc actctcttcc     120
ccttttcctg tgtttttgta gtgaagagac ctgaaagaaa aaagtaggga gaacataatg     180
agaacaaata cggtaatctc ttcatttgct agttcaagtg ctggacttgg gacttaggag     240
gggcaatgga gccgcttagt gcctacatct gacttggact gaaatatagg tgagagacaa     300
gattgtctca tatccgggga aatcataacc tatgactagg acgggaagag gaagcactgc     360
ctttacttca gtgggaatct cggcctcagc ctgcaagcca agtgttcaca gtgagaaaag     420
caagagaata agctaatact cctgtcctga acaaggcagc ggctccttgg taaagctact     480
ccttgatcga tc ctt tgc acc gga ttg ttc aaa gtg gac ccc agg gga gaa    531
            Leu Cys Thr Gly Leu Phe Lys Val Asp Pro Arg Gly Glu
              1               5                  10 gtc gga gca aag aac tta cca cca agc agt cca aga ggc cca gaa gca        579
Val Gly Ala Lys Asn Leu Pro Pro Ser Ser Pro Arg Gly Pro Glu Ala
     15                  20                  25 aac ctg gag gtg aga ccc aaa gaa agc tgg aac cat gct gac ttt gta        627
Asn Leu Glu Val Arg Pro Lys Glu Ser Trp Asn His Ala Asp Phe Val
 30                  35                  40                  45
```

```
cac tgt gag gac aca gag tct gtt cct gga aag ccc agt gtc aac gca       675
His Cys Glu Asp Thr Glu Ser Val Pro Gly Lys Pro Ser Val Asn Ala
             50                  55                  60 gat gag gaa gtc gga ggt ccc caa atc tgc cgt gta tgt ggg gac aag       723
Asp Glu Glu Val Gly Gly Pro Gln Ile Cys Arg Val Cys Gly Asp Lys
         65                  70                  75 gcc act ggc tat cac ttc aat gtc atg aca tgt gaa gga tgc aag ggc       771
Ala Thr Gly Tyr His Phe Asn Val Met Thr Cys Glu Gly Cys Lys Gly
     80                  85                  90 ttt ttc agg agg gcc atg aaa cgc aac gcc cgg ctg agg tgc ccc ttc       819
Phe Phe Arg Arg Ala Met Lys Arg Asn Ala Arg Leu Arg Cys Pro Phe
 95                 100                 105 cgg aag ggc gcc tgc gag atc acc cgg aag acc cgg cga cag tgc cag       867
Arg Lys Gly Ala Cys Glu Ile Thr Arg Lys Thr Arg Arg Gln Cys Gln
110                 115                 120                 125 gcc tgc cgc ctg cgc aag tgc ctg gag agc ggc atg aag aag gag atg       915
Ala Cys Arg Leu Arg Lys Cys Leu Glu Ser Gly Met Lys Lys Glu Met
                130                 135                 140 atc atg tcc gac gag gcc gtg gag gag agg cgg gcc ttg atc aag cgg       963
Ile Met Ser Asp Glu Ala Val Glu Glu Arg Arg Ala Leu Ile Lys Arg
            145                 150                 155 aag aaa agt gaa cgg aca ggg act cag cca ctg gga gtg cag ggg ctg      1011
Lys Lys Ser Glu Arg Thr Gly Thr Gln Pro Leu Gly Val Gln Gly Leu
        160                 165                 170 aca gag gag cag cgg atg atg atc agg gag ctg atg gac gct cag atg      1059
Thr Glu Glu Gln Arg Met Met Ile Arg Glu Leu Met Asp Ala Gln Met
    175                 180                 185 aaa acc ttt gac act acc ttc tcc cat ttc aag aat ttc cgg ctg cca      1107
Lys Thr Phe Asp Thr Thr Phe Ser His Phe Lys Asn Phe Arg Leu Pro
190                 195                 200                 205 ggg gtg ctt agc agt ggc tgc gag ttg cca gag cct ctg cag gcc cca      1155
Gly Val Leu Ser Ser Gly Cys Glu Leu Pro Glu Pro Leu Gln Ala Pro
                210                 215                 220 tcg agg gaa gaa gct gcc aag tgg agc cag gtc cgg aaa gat ctg tgc      1203
Ser Arg Glu Glu Ala Ala Lys Trp Ser Gln Val Arg Lys Asp Leu Cys
            225                 230                 235 tct ttg aag gtc tct ctg caa gct gcg ggg gga gga tgg cag tgt ctg      1251
Ser Leu Lys Val Ser Leu Gln Ala Ala Gly Gly Gly Trp Gln Cys Leu
        240                 245                 250 gaa cta caa acn ccc agc cga cag tgg cgg aaa gag atc ttc tcc ctg      1299
Glu Leu Gln Xaa Pro Ser Arg Gln Trp Arg Lys Glu Ile Phe Ser Leu
    255                 260                 265 ctg ccc cac atg gct gac atg tca acc tac atg ttc aaa ggc atc atc      1347
Leu Pro His Met Ala Asp Met Ser Thr Tyr Met Phe Lys Gly Ile Ile
270                 275                 280                 285 agc ttt gcc aaa gtc atc tcc tac ttc agg gac ttg ccc atc gag gac      1395
Ser Phe Ala Lys Val Ile Ser Tyr Phe Arg Asp Leu Pro Ile Glu Asp
                290                 295                 300 cag atc tcc ctg ctg aag ggg gcc gct ttc gag ctg tgt caa ctg aga      1443
Gln Ile Ser Leu Leu Lys Gly Ala Ala Phe Glu Leu Cys Gln Leu Arg
            305                 310                 315 ttc aac aca gtg ttc aac gcg gag act gga acc tgg gag tgt ggc cgg      1491
Phe Asn Thr Val Phe Asn Ala Glu Thr Gly Thr Trp Glu Cys Gly Arg
        320                 325                 330 ctg tcc tac tgc ttg gaa gac act gca ggt ggc ttc caa caa ctt cta      1539
Leu Ser Tyr Cys Leu Glu Asp Thr Ala Gly Gly Phe Gln Gln Leu Leu
    335                 340                 345 ctg gag ccc atg ctg aaa ttc cac tac atg ctg aag aag ctg cag ctg      1587
Leu Glu Pro Met Leu Lys Phe His Tyr Met Leu Lys Lys Leu Gln Leu
```

-continued

```
              350                 355                 360                 365
cat gag gag gag tat gtg ctg atg cag gcc atc tcc ctc ttc tcc cca          1635
His Glu Glu Glu Tyr Val Leu Met Gln Ala Ile Ser Leu Phe Ser Pro
                    370                 375                 380 gac cgc cca ggt gtg ctg cag cac cgc gtg gtg gac cag ctg cag gag          1683
Asp Arg Pro Gly Val Leu Gln His Arg Val Val Asp Gln Leu Gln Glu
                385                 390                 395 caa ttc gcc att act ctg aag tcc tac att gaa tgc aat cgg ccc cag          1731
Gln Phe Ala Ile Thr Leu Lys Ser Tyr Ile Glu Cys Asn Arg Pro Gln
            400                 405                 410 cct gct cat agg ttc ttg ttc ctg aag atc atg gct atg ctc acc gag          1779
Pro Ala His Arg Phe Leu Phe Leu Lys Ile Met Ala Met Leu Thr Glu
        415                 420                 425 ctc cgc agc atc aat gct cag cac acc cag cgg ctg ctg cgc atc cag          1827
Leu Arg Ser Ile Asn Ala Gln His Thr Gln Arg Leu Leu Arg Ile Gln
430                 435                 440                 445 gac ata cac ccc ttt gct acg ccc ctc atg cag gag ttg ttc ggc atc          1875
Asp Ile His Pro Phe Ala Thr Pro Leu Met Gln Glu Leu Phe Gly Ile
                    450                 455                 460 aca ggt agc tgagcggctg ccttgggtga caccttcgag aggcagccag                  1924
Thr Gly Ser acccagagcc ctctgagccg gcactcccgg gccaagacag atggacactg ccaagagccg        1984
acaatgccct gctggcctgt ctccctaggg aattcctgct atgacagctg gctagcattc       2044
ctcaggaagg acatggggtg cccc                                               2068
```

<210> SEQ ID NO 2
<211> LENGTH: 464
<212> TYPE: PRT
<213> ORGANISM: Homo sapiens
<220> FEATURE:
<223> OTHER INFORMATION: Xaa is threonine

<400> SEQUENCE: 2

```
Leu Cys Thr Gly Leu Phe Lys Val Asp Pro Arg Gly Glu Val Gly Ala
1               5                   10                  15

Lys Asn Leu Pro Pro Ser Ser Pro Arg Gly Pro Glu Ala Asn Leu Glu
                20                  25                  30

Val Arg Pro Lys Glu Ser Trp Asn His Ala Asp Phe Val His Cys Glu
            35                  40                  45

Asp Thr Glu Ser Val Pro Gly Lys Pro Ser Val Asn Ala Asp Glu Glu
        50                  55                  60

Val Gly Gly Pro Gln Ile Cys Arg Val Cys Gly Asp Lys Ala Thr Gly
65                  70                  75                  80

Tyr His Phe Asn Val Met Thr Cys Glu Gly Cys Lys Gly Phe Phe Arg
                85                  90                  95

Arg Ala Met Lys Arg Asn Ala Arg Leu Arg Cys Pro Phe Arg Lys Gly
                100                 105                 110

Ala Cys Glu Ile Thr Arg Lys Thr Arg Arg Gln Cys Gln Ala Cys Arg
            115                 120                 125

Leu Arg Lys Cys Leu Glu Ser Gly Met Lys Lys Glu Met Ile Met Ser
        130                 135                 140

Asp Glu Ala Val Glu Glu Arg Arg Ala Leu Ile Lys Arg Lys Lys Ser
145                 150                 155                 160

Glu Arg Thr Gly Thr Gln Pro Leu Gly Val Gln Gly Leu Thr Glu Glu
                165                 170                 175

Gln Arg Met Met Ile Arg Glu Leu Met Asp Ala Gln Met Lys Thr Phe
```

-continued

```
                180                 185                 190
Asp Thr Thr Phe Ser His Phe Lys Asn Phe Arg Leu Pro Gly Val Leu
                195                 200                 205
Ser Ser Gly Cys Glu Leu Pro Glu Pro Leu Gln Ala Pro Ser Arg Glu
210                 215                 220
Glu Ala Ala Lys Trp Ser Gln Val Arg Lys Asp Leu Cys Ser Leu Lys
225                 230                 235                 240
Val Ser Leu Gln Ala Ala Gly Gly Trp Gln Cys Leu Glu Leu Gln
                245                 250                 255
Xaa Pro Ser Arg Gln Trp Arg Lys Glu Ile Phe Ser Leu Leu Pro His
                260                 265                 270
Met Ala Asp Met Ser Thr Tyr Met Phe Lys Gly Ile Ile Ser Phe Ala
                275                 280                 285
Lys Val Ile Ser Tyr Phe Arg Asp Leu Pro Ile Glu Asp Gln Ile Ser
                290                 295                 300
Leu Leu Lys Gly Ala Ala Phe Glu Leu Cys Gln Leu Arg Phe Asn Thr
305                 310                 315                 320
Val Phe Asn Ala Glu Thr Gly Thr Trp Glu Cys Gly Arg Leu Ser Tyr
                325                 330                 335
Cys Leu Glu Asp Thr Ala Gly Gly Phe Gln Gln Leu Leu Glu Pro
                340                 345                 350
Met Leu Lys Phe His Tyr Met Leu Lys Lys Leu Gln Leu His Glu Glu
                355                 360                 365
Glu Tyr Val Leu Met Gln Ala Ile Ser Leu Phe Ser Pro Asp Arg Pro
                370                 375                 380
Gly Val Leu Gln His Arg Val Val Asp Gln Leu Gln Glu Gln Phe Ala
385                 390                 395                 400
Ile Thr Leu Lys Ser Tyr Ile Glu Cys Asn Arg Pro Gln Pro Ala His
                405                 410                 415
Arg Phe Leu Phe Leu Lys Ile Met Ala Met Leu Thr Glu Leu Arg Ser
                420                 425                 430
Ile Asn Ala Gln His Thr Gln Arg Leu Leu Arg Ile Gln Asp Ile His
                435                 440                 445
Pro Phe Ala Thr Pro Leu Met Gln Glu Leu Phe Gly Ile Thr Gly Ser
450                 455                 460
```

<210> SEQ ID NO 3
<211> LENGTH: 25
<212> TYPE: DNA
<213> ORGANISM: Artificial Sequence
<220> FEATURE:
<223> OTHER INFORMATION: putative SXR response element from the steroid
      hydoxylase, rCYP3A1

<400> SEQUENCE: 3
tagacagttc atgaagttca tctac                                         25

<210> SEQ ID NO 4
<211> LENGTH: 25
<212> TYPE: DNA
<213> ORGANISM: Artificial Sequence
<220> FEATURE:
<223> OTHER INFORMATION: putative SXR response element from the steroid
      hydoxylase, rCYP3A2

<400> SEQUENCE: 4
taagcagttc ataaagttca tctac                                         25

```
<210> SEQ ID NO 5
<211> LENGTH: 25
<212> TYPE: DNA
<213> ORGANISM: Artificial Sequence
<220> FEATURE:
<223> OTHER INFORMATION: putative SXR response element from the steroid
      hydoxylase, rUGT1A6

<400> SEQUENCE: 5
actgtagttc ataaagttca catgg                                              25

<210> SEQ ID NO 6
<211> LENGTH: 26
<212> TYPE: DNA
<213> ORGANISM: Artificial Sequence
<220> FEATURE:
<223> OTHER INFORMATION: putative SXR response element from the steroid
      hydoxylase, rbCYP2C1

<400> SEQUENCE: 6
caatcagttc aacagggttc accaat                                             26

<210> SEQ ID NO 7
<211> LENGTH: 33
<212> TYPE: DNA
<213> ORGANISM: Artificial Sequence
<220> FEATURE:
<223> OTHER INFORMATION: putative SXR response element from the steroid
      hydoxylase, rP450R

<400> SEQUENCE: 7
cacaggtgag ctgaggccag cagcaggtcg aaa                                     33

<210> SEQ ID NO 8
<211> LENGTH: 27
<212> TYPE: DNA
<213> ORGANISM: Artificial Sequence
<220> FEATURE:
<223> OTHER INFORMATION: putative SXR response element from the steroid
      hydoxylase, rCYP2A1

<400> SEQUENCE: 8
gtgcaggttc aactggaggt caacatg                                            27

<210> SEQ ID NO 9
<211> LENGTH: 27
<212> TYPE: DNA
<213> ORGANISM: Artificial Sequence
<220> FEATURE:
<223> OTHER INFORMATION: putative SXR response element from the steroid
      hydoxylase, rCYP2A2

<400> SEQUENCE: 9
gtgctggttc aactggaggt cagtatg                                            27

<210> SEQ ID NO 10
<211> LENGTH: 27
<212> TYPE: DNA
<213> ORGANISM: Artificial Sequence
<220> FEATURE:
<223> OTHER INFORMATION: putative SXR response element from the steroid
      hydoxylase, rCYP2C6

<400> SEQUENCE: 10
agtctagttc agtgggggtt cagtctt                                            27
```

<210> SEQ ID NO 11
<211> LENGTH: 27
<212> TYPE: DNA
<213> ORGANISM: Artificial Sequence
<220> FEATURE:
<223> OTHER INFORMATION: putative SXR response element from the steroid
      hydoxylase, hCYP2E1

<400> SEQUENCE: 11
gagatggttc aaggaagggt cattaac                                    27

<210> SEQ ID NO 12
<211> LENGTH: 26
<212> TYPE: DNA
<213> ORGANISM: Artificial Sequence
<220> FEATURE:
<223> OTHER INFORMATION: direct repeat with spacer of 0 nucleotides

<400> SEQUENCE: 12
catagtcagg tcaaggtcag atcaac                                     26

<210> SEQ ID NO 13
<211> LENGTH: 27
<212> TYPE: DNA
<213> ORGANISM: Artificial Sequence
<220> FEATURE:
<223> OTHER INFORMATION: direct repeat with spacer of 1 nucleotides

<400> SEQUENCE: 13
catagtcagg tcataggtca gatcaac                                    27

<210> SEQ ID NO 14
<211> LENGTH: 28
<212> TYPE: DNA
<213> ORGANISM: Artificial Sequence
<220> FEATURE:
<223> OTHER INFORMATION: direct repeat with spacer of 2 nucleotides

<400> SEQUENCE: 14
catagtcagg tcaataggtc agatcaac                                   28

<210> SEQ ID NO 15
<211> LENGTH: 29
<212> TYPE: DNA
<213> ORGANISM: Artificial Sequence
<220> FEATURE:
<223> OTHER INFORMATION: direct repeat with spacer of 3 nucleotides

<400> SEQUENCE: 15
catagtcagg tcatataggt cagatcaac                                  29

<210> SEQ ID NO 16
<211> LENGTH: 30
<212> TYPE: DNA
<213> ORGANISM: Artificial Sequence
<220> FEATURE:
<223> OTHER INFORMATION: direct repeat with spacer of 4 nucleotides

<400> SEQUENCE: 16
catagtcagg tcatataagg tcagatcaac                                 30

<210> SEQ ID NO 17
<211> LENGTH: 31
<212> TYPE: DNA
<213> ORGANISM: Artificial Sequence
<220> FEATURE:
<223> OTHER INFORMATION: direct repeat with spacer of 5 nucleotides -continued

```
<400> SEQUENCE: 17
catagtcagg tcatatatag gtcagatcaa c                                    31

<210> SEQ ID NO 18
<211> LENGTH: 33
<212> TYPE: DNA
<213> ORGANISM: Artificial Sequence
<220> FEATURE:
<223> OTHER INFORMATION: direct repeat with spacer of 6 nucleotides

<400> SEQUENCE: 18
catagtcagg tcatatataa ggtcaagatc aac                                  33

<210> SEQ ID NO 19
<211> LENGTH: 33
<212> TYPE: DNA
<213> ORGANISM: Artificial Sequence
<220> FEATURE:
<223> OTHER INFORMATION: direct repeat with spacer of 7 nucleotides

<400> SEQUENCE: 19
catagtcagg tcatatatat aggtcagatc aac                                  33

<210> SEQ ID NO 20
<211> LENGTH: 36
<212> TYPE: DNA
<213> ORGANISM: Artificial Sequence
<220> FEATURE:
<223> OTHER INFORMATION: direct repeat with spacer of 10 nucleotides

<400> SEQUENCE: 20
catagtcagg tcatatatat ataaggtcag atcaac                               36

<210> SEQ ID NO 21
<211> LENGTH: 41
<212> TYPE: DNA
<213> ORGANISM: Artificial Sequence
<220> FEATURE:
<223> OTHER INFORMATION: direct repeat with spacer of 15 nucleotides

<400> SEQUENCE: 21
catagtcagg tcatagtagt agtagtagag gtcagatcaa c                         41
```

STEROID-ACTIVATED NUCLEAR RECEPTORS AND USES THEREFOR

This invention was made with Government support under Grant No. GM-26444, awarded by the National Institute of Health. The Government has certain rights in the invention.

FIELD OF THE INVENTION

The present invention relates to intracellular receptors, nucleic acids encoding same, and uses therefor. In a particular aspect, the present invention relates to methods for the modulation of physiological response to elevated levels of steroids and steroid-like compounds.

BACKGROUND OF THE INVENTION

Nuclear receptors constitute a large superfamily of ligand-dependent and sequence-specific transcription factors. Members of this family influence transcription either directly, through specific binding to the promoters of target genes (see Evans, in *Science* 240:889–895 (1988)), or indirectly, via protein-protein interactions with other transcription factors (see, for example, Jonat et al., in *Cell* 62:1189–1204 (1990), Schuele et al., in *Cell* 62:1217–1226 (1990), and Yang-Yen et al., in *Cell* 62:1205–1215 (1990)). The nuclear receptor superfamily (also known in the art as the "steroid/thyroid hormone receptor superfamily") includes receptors for a variety of hydrophobic ligands, including cortisol, aldosterone, estrogen, progesterone, testosterone, vitamin $D_3$, thyroid hormone and retinoic acid, as well as a number of receptor-like molecules, termed "orphan receptors" for which the ligands remain unknown (see Evans, 1988, supra). These receptors all share a common structure indicative of divergence from an ancestral archetype.

Lipophilic hormones such as steroids, retinoic acid, thyroid hormone, and vitamin D3 control broad aspects of animal growth, development and adult organ physiology. The effects of these hormones are mediated by members of the nuclear receptor superfamily. The nuclear receptors for such non-steroidal compounds as thyroid hormone (TR), vitamin D3 (VDR), all-trans retinoic acid (RAR), fatty acids and eicosanoids (PPAR) form heterodimers with the 9-cis retinoic acid receptor (RXR) that bind bipartite hormone-response elements (HREs) composed of directly repeated half sites related to the sequence AGGTCA (see, for example, Mangelsdorf and Evans in *Cell* 83:841 (1995)).

In contrast, nuclear receptors for steroidal compounds function as homodimers and bind to palindromic target sequences spaced by three nucleotides (see, for example, Beato et al. in *Cell* 83:851 (1995)). In addition to the known receptors, a large group of structurally-related "orphan" nuclear receptors has been described which possess obvious DNA and ligand binding domains but lack identified ligands (see, for example, Mangelsdorf et al., in *Cell* 83:835 (1995); Enmark and Gustafsson in *Mol. Endocrinol.* 10:1293 (1996); and O'Malley and Conneely in *Mol. Endocrinol.* 6:1359 (1992)). Each has the potential to regulate a distinct endocrine signaling pathway.

It is widely viewed that the hormone response is a consequence of the release, from an endocrine gland, of a ligand that circulates through the blood, and coordinately regulates responses in target tissues by acting through specific nuclear receptors. Hormone responsiveness is dependent on the ability to rapidly clear ligand from the blood and the body so that, in the absence of a stimulus, target tissues return to a ground state. Hormonal homeostasis is thus achieved by the coordinated release and degradation of bioactive hormones.

Steroid hormones and their many metabolites are primarily inactivated by reduction and oxidation in the liver. Since literally hundreds of adrenal steroids have been identified (e.g., dozens of each of the sex steroids (androgens, estrogens and progestins), 25–35 vitamin D metabolites, and likely hundreds of fatty acids, eicosanoids, hydroxyfats and related bioactive lipids), the problem of efficient ligand elimination is critical to physiologic homeostasis. In addition to the existence of a myriad of endogenous hormones, a similar diversity of ingested plant and animal steroids and bioactive xenobiotic compounds must also be degraded.

Selye first introduced the concept that exogenous steroids and pharmacologic substances may function to modulate the expression of enzymes that would protect against subsequent exposure to toxic xenobiotic substances (see Selye in *J. Pharm. Sci.* 60:1 (1971)). These compounds, which Selye called "catatoxic steroids" are typified by the synthetic glucocorticoid antagonist, pregnenolone-16-carbonitrile (PCN). PCN, and a variety of xenobiotic steroids, induce the proliferation of hepatic endoplasmic reticulum and the expression of cytochrome P450 genes (see, for example, Burger et al., in *Proc. Natl. Acad. Sci.* (USA) 89:2145 (1992); Gonzalez et al., in *Mol. Cell. Biol.* 6:2969 (1986); and Schuetz and Guzelian in *J. Biol. Chem.* 259:2007 (1984)). One consequence of such regulation is the induction of nonspecific "protection" against such diverse xenobiotic compounds as digitoxin, indomethacin, barbiturates and steroids.

Insight into the mechanism by which PCN exerts its catatoxic effects is provided by the demonstration that PCN induces the expression of CYP3A1 and CYP3A2, two closely related members of the P450 family of monooxygenases (see, for example, Elshourbagy and Guzelian in *J. Biol. Chem.* 255:1279 (1980); Heuman et al., in *Mol. Pharmacol.* 21:753 (1982); Hardwick et al., in *J. Biol. Chem.* 258:10182 (1983); Scheutz and Guzelian in *J. Biol. Chem.* 259:2007 (1984); Scheutz et al., in *J. Biol. Chem.* 259:1999 (1984); and Gonzalez et al., in *J. Biol. Chem.* 260:7435 (1985)). The CYP3A hemoproteins display broad substrate specificity, hydroxylating a variety of xenobiotics (e.g., cyclosporin, warfarin and erythromycin), as well as endogenous steroids (e.g., cortisol, progesterone, testosterone and DHEA-sulfate. See, for example, Nebert and Gonzalez in *Ann. Rev. Biochem.* 56:945 (1987) and Juchau in *Life Sci.* 47:2385 (1990)). A PCN response element (which is highly conserved in the CYP3A2 gene promoter) has since been identified in subsequent studies with the cloned CYP3A1 gene promoter (see Miyata et al., in *Archives Biochem. Biophysics* 318:71 (1995) and Quattrochi et al., in *J. Biol. Chem.* 270:28917 (1995)). This response element comprises a direct repeat of two copies of the nuclear receptor half-site consensus sequence AGTTCA.

In addition to inducing CYP3A gene expression, PCN has also been shown to have marked effects on hepatic cholesterol homeostasis. These effects include significant decreases in the levels of HMG-CoA reductase and cholesterol 7α-hydroxylase gene expression, with associated reductions in sterol biosynthesis and bile acid secretion. PCN has also been reported to enhance the formation of cholesterol esters and the hypersecretion of cholesterol into the bile. Thus, PCN affects key aspects of cholesterol metabolism, including its biosynthesis, storage and secretion.

While it appears that catatoxic steroids regulate the expression of cytochromes and other detoxifying enzymes, two lines of evidence argue that such regulation is independent of the classical steroid receptors. First, many of the most potent compounds (e.g., PCN, spironolactone, cyproterone acetate) are steroid receptor antagonists, whereas other potent compounds (e.g., dexamethasone) are receptor agonists (see, for example, Burger et al., supra). Second, the nonspecific protective response remains after bilateral adrenalectomy (and presumably in the absence of most adrenal steroids) but not after partial hepatectomy (see, for example, Selye, supra)

Activation of orphan nuclear receptor(s) by catatoxic steroids provides a possible mechanism for the induction of xenobiotic metabolizing enzymes by compounds that do not activate known steroid receptors. Because such enzymes are activated by high (pharmacological) doses of xenobiotic and natural steroids, such a "sensor" would be expected to be a broad-specificity, low-affinity receptor. Such receptors could be activated not only by endogenous steroids and metabolites but also by exogenous compounds such as phytosteroids, xenobiotics and pharmacologic inducers. Indeed, it is known that a variety of such compounds can activate P450 genes responsible for their detoxification or degradation (see, for example, Fernandez-Salguero and Gonzalez in *Pharmacogenetics* 5:S123 (1995); Denison and Whitlock, Jr. in *J. Biol. Chem.* 270:18175 (1995); Hankinson in *Ann. Rev. Pharmacol. Toxicol.* 35:307 (1995); and Rendic and Di Carlo in *Drug Metab. Rev.* 29:413 (1997)).

Accordingly, there is still a need in the art for the identification and characterization of broad specificity, low affinity receptors which participate in the mediation of the physiological effect(s) of hormones.

BRIEF DESCRIPTION OF THE INVENTION

In accordance with the present invention, we have isolated and characterized an example of a novel class of nuclear receptor(s), termed the steroid X receptor (SXR). SXR is expressed almost exclusively in the liver, the primary site of xenobiotic and steroid catabolism. Unlike classical steroid receptors, SXR heterodimerizes with RXR and binds to directly repeated sequences related to the half-site, AGT-TCA. SXR can activate transcription through response elements found in some steroid inducible P450 genes in response to a wide variety of natural and synthetic steroid hormones, including antagonists such as PCN—ideal properties for a "steroid sensing receptor" which mediates the physiological effect(s) of hormones. SXR represents the first new class of steroid receptors described since the identification of the mineralocorticoid receptor ten years ago.

In accordance with a particular aspect of the present invention, there are also provided nucleic acid sequences encoding the above-identified receptors, as well as constructs and cells containing same, and probes derived therefrom. Furthermore, it has also been discovered that a wide variety of substrates modulate the transcription activating effects of invention receptors.

the base vector is tk-luc in all cases (see Hollenberg et al., in Nature 318:635 (1985)):
DR-1 response element, tk(ApoAI)$_4$ (see Ladias and Karathanasis in *Science* 251:561 (1991));
DR-2 response element, tk(Hox-B1-RARE)$_2$ (see Ogura and Evans in *Proc. Natl. Acad. Sci.* (USA) 92:387 (1995));
βDR-3 response element, tk(SPP)$_2$ (see Umesono et al., in *Cell* 65:1255 (1991)),
DR-4 response element, tk(MLV-TRE)$_2$ (see Umesono et al, supra);
βDR-4 response element, tk(LXRE) $_3$ (see Willy et al., supra);
βDR-5 response element, tk(βRARE)$_3$ (see Sucov et al., in *Proc. Natl. Acad. Sci.* (U.S.A.) 87:5392 (1990));
TREp response element, tk(TRE$_p$)$_2$ (see Umesono et al. supra).

The data shown are expressed as mean fold induction over solvent control ± standard error from triplicate assays.

Figure 5:
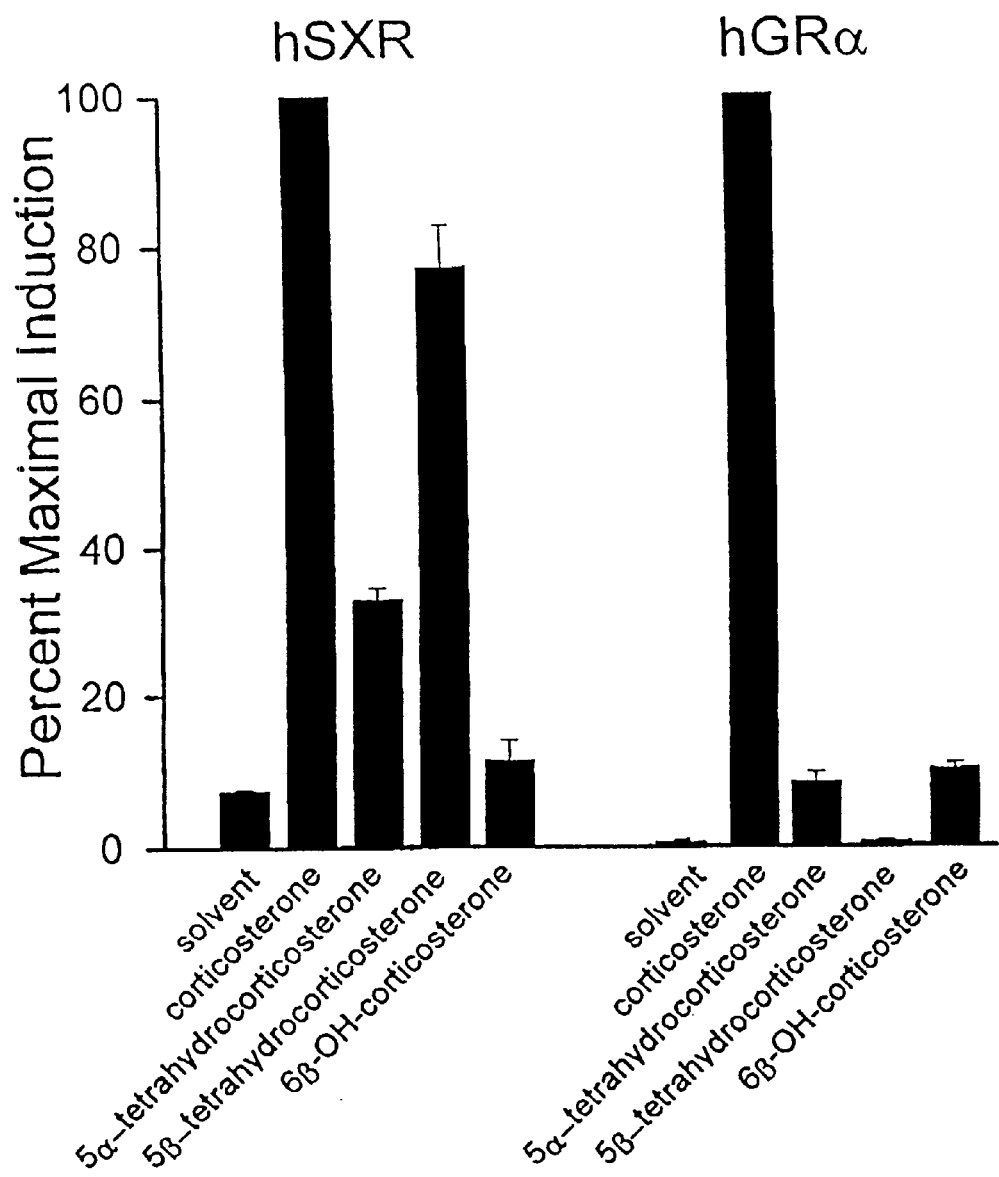

FIG. 5 further illustrates the broad ligand specificity of SXR. Thus, it is seen that reduction of the 4–5 double bond does not inactivate corticosterone. 6b-hydroxylated, non-reduced, 5α and 5β reduced forms of corticosterone were tested for their ability to activate GAL-SXR on tk(MH100)$_4$-luc and hGRα on MTV-luc at 50 μM. Similar results were obtained using full-length SXR.

DETAILED DESCRIPTION OF THE INVENTION

In accordance with the present invention, we have identified a new class of receptors which are part of the steroid/ thyroid hormone superfamily of receptors, a representative member of which has been designated SXR (or "steroid X receptor"). Invention receptors are characterized by:

forming a heterodimer with retinoid X receptor (RXR),
binding to a (direct or inverted) repeat response element motif based on the half site AGTTCA,
activating transcription through response elements found in steroid inducible P450 genes in response to a wide variety of natural and synthetic steroid hormones, and
being prominently expressed in the liver and the intestine.

Invention receptor(s) comprise a protein of approximately 464 amino acids (see SEQ ID NO:2), which is most closely, although distantly, related to the Xenopus benzoate X receptor (BXR), the vitamin D3 receptor (VDR) and the constitutively activated receptor (CAR). Also provided herein is a 2068 bp cDNA which encodes an example of invention receptors (see SEQ ID NO:1).

Invention receptor can be further characterized as having a DNA binding domain of about 67 amino acids with 9 Cys residues (i.e., amino acid residues 71–137, as set forth in SEQ ID NO:2), wherein the SXR DNA binding domain has about 73% amino acid identity with the DNA binding domain of the Xenopus benzoate X receptor. Alternatively, or in addition, invention receptor can be further characterized as having a ligand binding domain of at least about 198 amino acids (i.e., at least amino acid residues 267–464, as set forth in SEQ ID NO:2), wherein said ligand binding domain has about 52% amino acid identity with the ligand binding domain of the Xenopus benzoate X receptor.

A presently preferred polypeptide according to the invention is a polypeptide having substantially the same amino acid sequence as shown in SEQ ID NO:2. As employed herein, the phrase "substantially the same," whether used in reference to the nucleotide sequence of DNA, the ribonucleotide sequence of RNA, or the amino acid sequence of protein, refers to sequences that have slight and non-consequential sequence variations from the actual sequences disclosed herein. Species that are substantially the same are considered to be equivalent to the disclosed sequences and as such are within the scope of the appended claims. In this regard, "slight and non-consequential sequence variations" mean that sequences that are substantially the same as the DNA, RNA, or proteins disclosed and claimed herein are functionally equivalent to the sequences disclosed and claimed herein. Functionally equivalent sequences will function in substantially the same manner to produce substantially the same compositions as the nucleic acid and amino acid compositions disclosed and claimed herein. In particular, functionally equivalent DNAs encode proteins that are the same as those disclosed herein or proteins that have conservative amino acid variations, such as substitution of a non-polar residue for another non-polar residue or a charged residue for a similarly charged residue. These changes include those recognized by those of skill in the art as those that do not substantially alter the tertiary structure of the protein.

An especially preferred polypeptide according to the invention is a polypeptide having the same amino acid sequence as shown in SEQ ID NO:2.

Also included within the scope of the present invention are functional fragments of the invention polypeptide(s). Such fragments include peptides having the DNA binding and/or the ligand binding properties of SXR, e.g., the DNA binding domain thereof (e.g., amino acid residues 71–137 as shown in SEQ ID NO:2), the ligand binding domain thereof (e.g., amino acid residues 267–464 as shown in SEQ ID NO:2).

Figure 1:
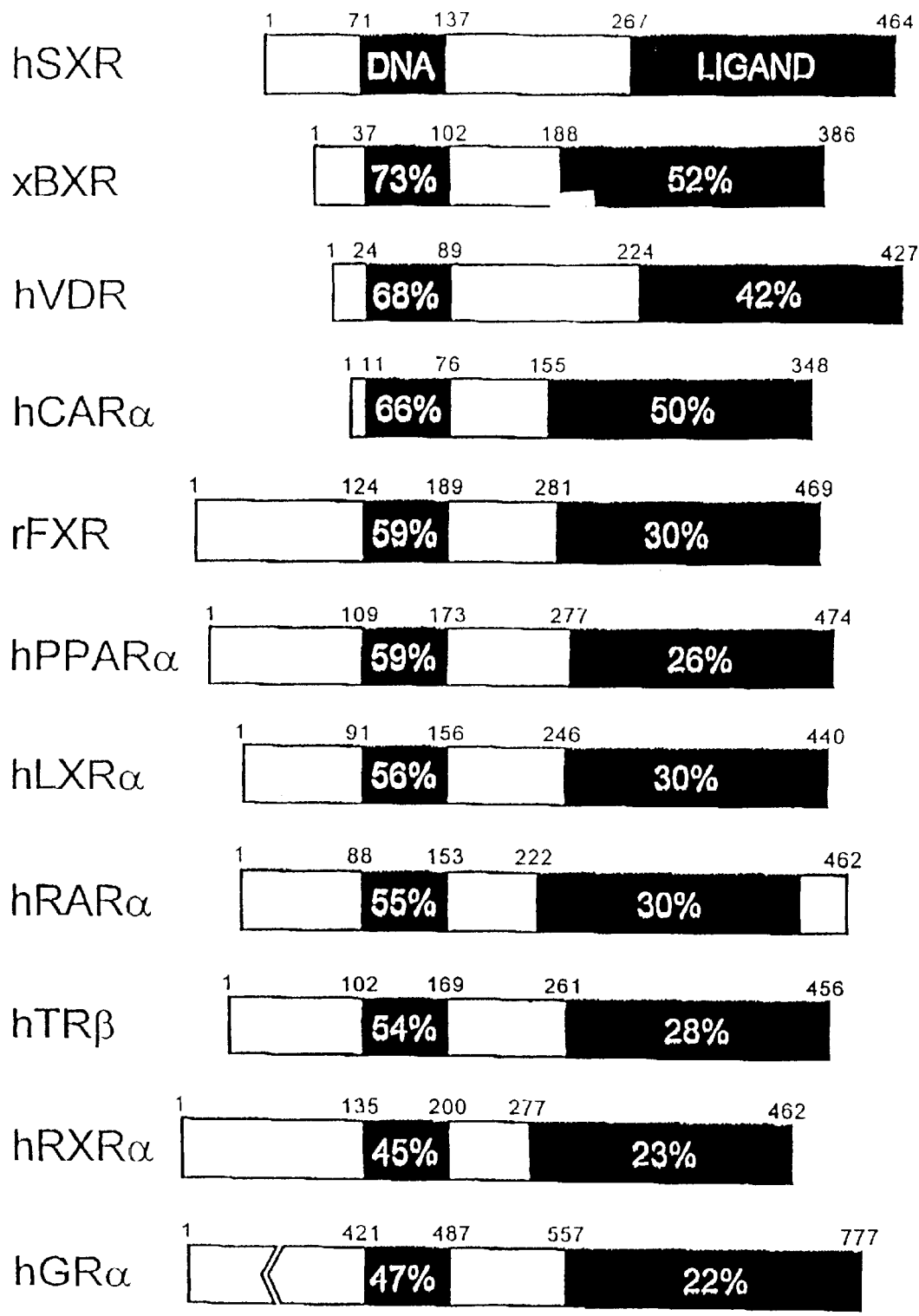
FIG. 1 presents a schematic comparison between SXR and other RXR partners (e.g., the Xenopus benzoate X receptor (xBXR), the human vitamin D3 receptor (hVDR), the human constitutively active receptor-alpha (hCARα), the rat farnesoid X receptor (rFXR), the human peroxisome proliferator activated receptor alpha (hPPARα), the human liver-derived receptor X (LXRα), the human retinoic acid receptor alpha (hPARα), the human thyroid hormone receptor beta (hTRβ), the human retinoid X receptor alpha (RXRα) and the human glucocorticoid receptor alpha (hGRα)). Amino acid sequences were aligned using the program GAP (see Devereaux et al., in *Nucl. Acids Res.* 12:387–395 (1984)). Similarity between RXR and other receptors is expressed as percent amino acid identity.

SXR was isolated in a screen to identify potential human homologs of the Xenopus benzoate 'X' receptor, BXR (also known as xONR-1) (see, for example, Smith et al., in *Nucl. Acids Res.* 22:66 (1994)). The cDNA encodes a predicted protein of 464 amino acids (see SEQ ID NO:2) which is most closely, although distantly, related to BXR (73% amino acid identity in the DNA-binding domain (DBD), 52% in the ligand binding domain (LBD)), the vitamin D3 receptor and the orphan receptor CAR (see Baes et al., in *Mol. Cell. Biol.* 14:1544 (1994); see FIG. 1). Besides these receptors, SXR shows no more similarity to other nuclear receptors than the different receptor subfamilies do to each other (see FIG. 1). Since true homologs among nuclear receptors typically share considerable similarity, especially in the DBD, SXR is clearly an example of a novel class of receptors within the nuclear receptor superfamily.

Northern blot analysis shows that SXR mRNA is expressed substantially exclusively in the liver and intestine (at high levels in liver and at more moderate levels in the intestine). Longer exposures did not reveal expression in any other tissues on these blots. Multiple mRNAs were detected, ranging from 3500 nt to larger than 9000 nt.

Electrophoretic mobility shift assays were employed to determine the ability of SXR to heterodimerize with RXR and to analyze the selectivity and specificity of SXR DNA binding (see Example 2). Receptors that heterodimerize with RXR typically bind to directly repeated sequences related to AGGTCA (see Mangelsdorf and Evans supra). Thus, SXR-:RXR heterodimers were tested on a series of related elements differing in the spacing between half sites from 0 to 15 nucleotides (see SEQ ID NOS:12–21). Strong binding was selective to a DR-4 motif, with minimal binding to DR-3 and DR-5 motifs, and substantially no binding to other spacing motifs. In contrast, when the related AGTTCA (βDR) half site was used, strong binding was seen on both βDR-4 and βDR-5 motifs, and significant, but reduced binding to the βDR-3 motif. These results demonstrate that SXR binds DNA as a heterodimer with RXR rather than as a homodimer like the classical steroid receptors (see Beato supra).

Figure 2:
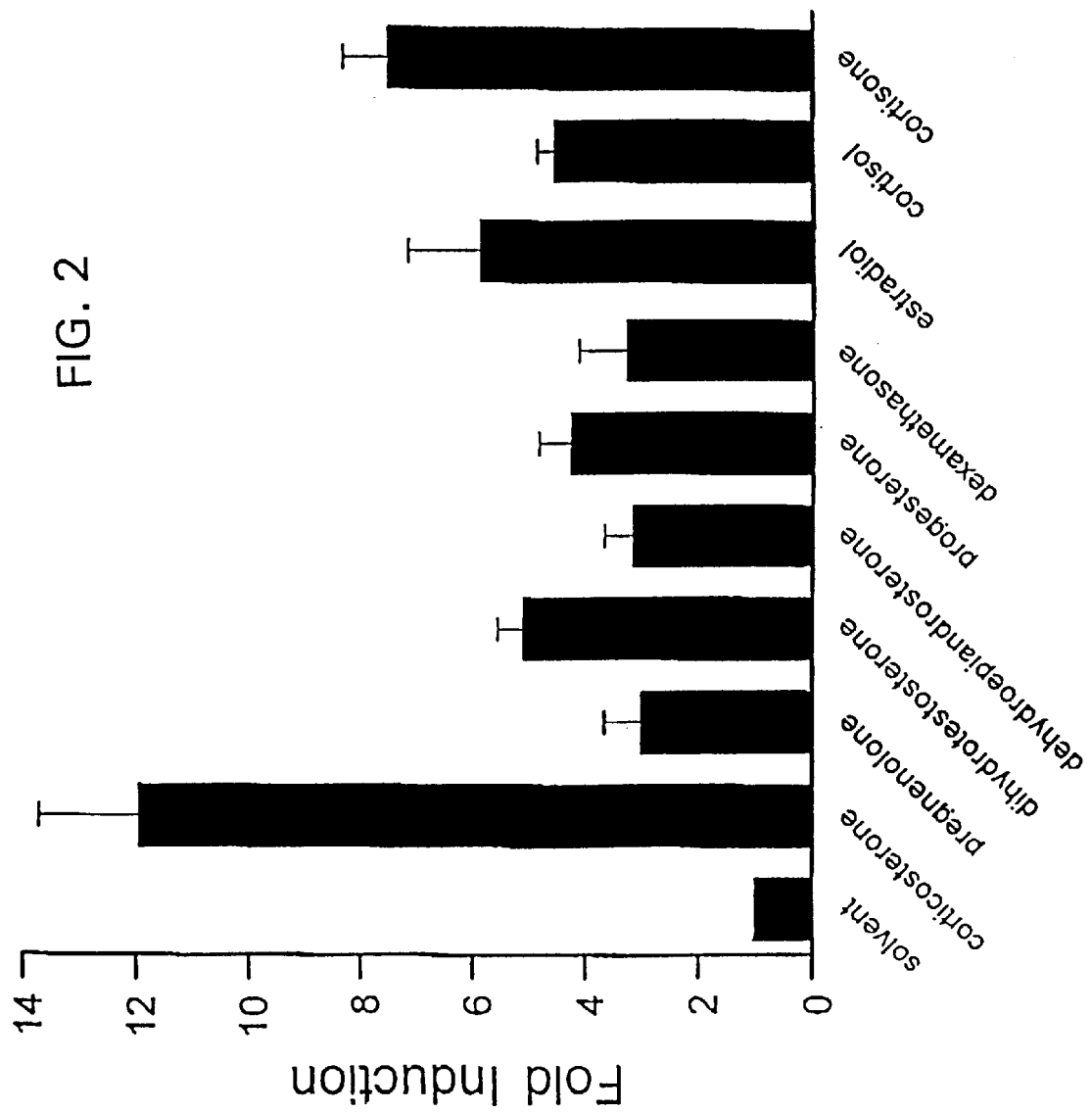
FIG. 2 demonstrates the broad ligand specificity of SXR. Thus, chimeric receptors composed of the GAL4 DNA-binding domain (DBD) and the SXR-ligand binding domain (LBD) were cotransfected into CV-1 cells with the reporter gene tk(MH100)$_4$-luc (see Forman et al., in *Cell* 81:541 (1995)). In oreliminary studies, DHEA and pregnenolone were found to activate this chimeric receptor, therefore other steroids were tested for activation as well. Results are shown in the Figure as fold induction over solvent (DMSO) control for 50 μM of steroid, and represent the averages and standard error from triplicate assays. Reporter alone or reporter plus GAL4-DBD were not activated by any of these compounds. Similar results were obtained using full-length receptors and appropriate reporters (see FIG. 3).

To determine whether the activity of SXR was ligand-dependent, mixtures of natural and synthetic compounds were tested for their ability to activate SXR in transfection-based assays (see Example 3). A mixture containing dehydroepiandrosterone (DHEA) and pregnenolone was observed to be active, suggesting that SXR might be a new steroid receptor. To characterize its response properties, a large variety of steroids, including intermediate and major products of known steroid biosynthetic pathways were tested. Surprisingly, most of these compounds were active, although there were clear differences in potency (see FIG. 2). Indeed, most of the more than 70 steroids tested showed some activity at high doses. Activation was dependent on the ligand binding domain of SXR since both full-length receptors and GAL4-receptor ligand binding domain chimeras showed similar activity, whereas there was no activation of reporter gene expression in experiments with reporter alone or reporter plus GAL4 DNA-binding domain.

The most potent and efficacious activator of the numerous steroids tested is corticosterone. Estradiol and dihydrotestosterone are also remarkably effective activators while aldosterone and 1,25 dihydroxy vitamin D3 are inactive, even at 50 μM. Although ligands for the classical steroid receptors do show some overlap in receptor specificity, there is no example of a nuclear receptor that can be activated by so many different types of steroids. This broad ligand specificity of SXR parallels that of PPARα, which can be activated by an extremely diverse group of dietary fatty acids at micromolar levels (see, for example, Forman et al., in *Proc. Natl. Acad. Sci.* USA 94:4312 (1997) and Gottlicher et al., in *Proc. Natl. Acad. Sci.* USA 89:4653 (1992)).

Figure 3:
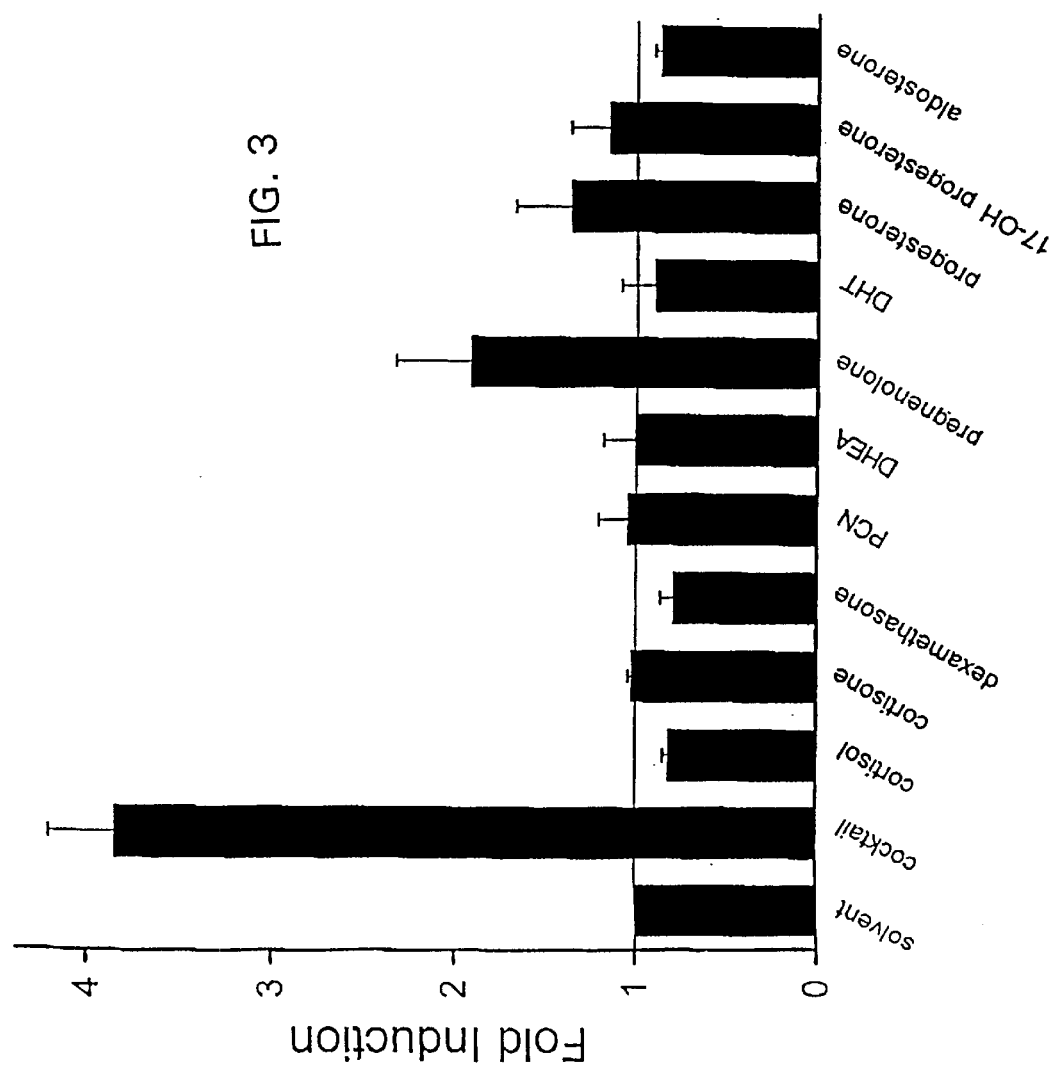
FIG. 3 illustrates the ability of steroidal activators to act additively. Thus, the ability of steroidal activators to act additively was tested using full-length SXR and the reporter tk(LXRE)$_3$-luc (see Willy et al., in *Genes Dev.* 9:1033 (1995)). The cocktail contained 10 μM of each steroid for an overall concentration of 100 μM total steroid. The cocktail and its individual components were tested at 100, 10 and 1 μM; results are shown in the Figure for 100 μM cocktail and 10 μM aliquots of the component steroids.

The diversity of steroids showing activity on SXR suggests that this novel class of receptors might be able to sense cumulative, as well as individual steroid levels, predicting that combinations of activators might be more active than the individual components. As shown in FIG. 3, a cocktail containing 10 steroids, each at 10 $\mu$M concentration (i.e., an overall steroid concentration of 100 $\mu$M), was considerably more active than its individual components at 10 $\mu$M, a concentration at which most were inactive. These results confirm that SXR is a broad-specificity, low-affinity, steroid-activated receptor.

An important requirement for physiologic homeostasis is the removal and detoxification of various endogenous hormones and xenobiotic compounds with biological activity. Much of the detoxification is performed by cytochrome P450 enzymes, many of which have broad substrate specificity and are inducible by a bewildering array of compounds, including steroids. The ingestion of dietary steroids and lipids induces the same enzymes and thus, must be integrated into a coordinated metabolic pathway. Instead of possessing hundreds of receptors, one for each inducing compound, the class of receptors described herein indicates the existence of a class of broad-specificity, low-affinity nuclear receptors that monitor total steroid levels and induce the expression of genes encoding xenobiotic metabolizing enzymes. These results indicate the existence of a steroid sensor mechanism for removal of elevated levels of steroids (or steroid-like compounds) from circulation via broad-specificity, low-affinity receptors which represent a novel branch of the nuclear receptor superfamily.

Indeed, a search of the GENBANK database for genes containing putative SXR response elements identified a number of steroid hydroxylases, e.g., CYP2A1, CYP2A2, CYP2C1, CYP2C6, CYP3A1, CYP3A2, P450 oxidoreductase and UDP-glucuronosyltransferase, as candidate target genes.

The relevant portions of these sequences are as follows:
DR-3
rCYP3A1 tagac AGTTCA tga AGTTCA tctac (SEQ ID NO:3)
rCYP3A2 taagc AGTTCA taa AGTTCA tctac (SEQ ID NO:4)
rUGT1A6 actgt AGTTCA taa AGTTCA catgg (SEQ ID NO:5)
DR-4
rbCYP2C1 caatc AGTTCA acag GGTTCA ccaat (SEQ ID NO:6)
rP450R cac AGGTGA gctg AGGCCA gcagc AGGTCG aaa (SEQ ID NO:7)
DR-5
rCYP2A1 gtgca GGTTCA actgg AGGTCA acatg (SEQ ID NO:8)
rCYP2A2 gtgct GGTTCA actgg AGGTCA gtatg (SEQ ID NO:9)
rCYP2C6 agtct AGTTCA gtggg GGTTCA gtctt (SEQ ID NO:10)
hCYP2E1 gagat GGTTCA aggaa GGGTCA ttaac (SEQ ID NO:11)

Figure 4:
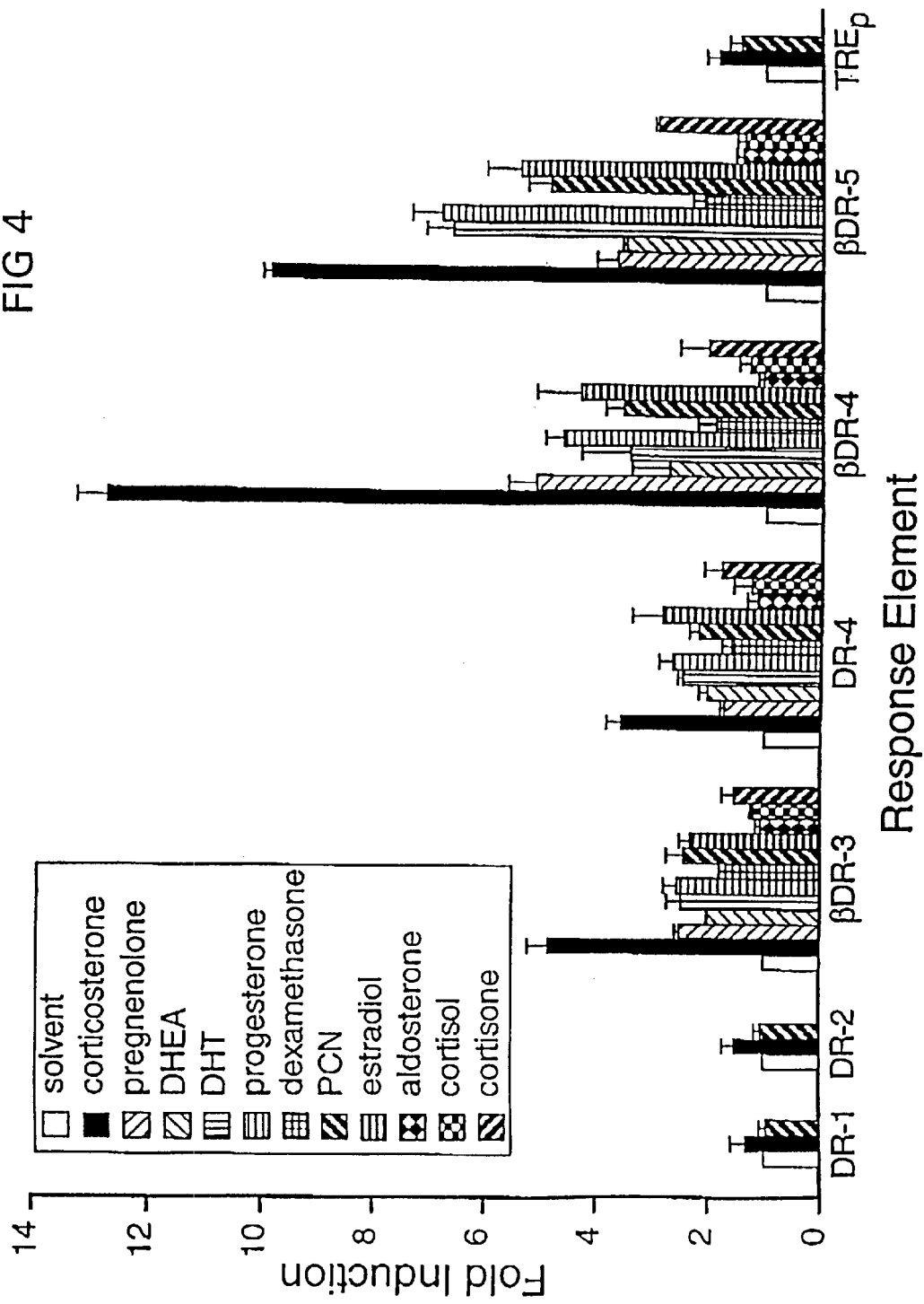
FIG. 4 illustrates the broad activator and response element specificity of SXR. Full-length SXR was tested in cotransfection experiments for its ability to activate elements similar to those in FIG. 3 in response to a panel of steroids at 50 μM. DR-1,2 and TREp were only very slightly activated, hence results are shown only for corticosterone and PCN. The actual response elements and the number of copies are as follows.

The data shown in FIG. 4 verify that SXR can activate DR-3, DR-4 and DR-5 elements that are present in these genes. In the series of transfections described in Example 3, corticosterone along with pregnenolone, progesterone, DHT, estradiol and PCN are consistently among the best activators. Dexamethasone, cortisone and DHEA are in the intermediate group with little response from either aldosterone or cortisol (see FIG. 4). Consistent with the DNA-binding data, maximal activities are achieved on $\beta$DR-3, $\beta$DR-4 and $\beta$DR-5 elements.

Thus, SXR response elements are found in genes encoding steroid hydroxylases, P450 oxidoreductase, and glucuronosyl transferase. These enzymes can metabolize endogenous as well as xenobiotic compounds and are legitimate targets for a receptor that is activated by pharmacological levels of steroids. SXR is highly expressed in liver, the major expression site of xenobiotic metabolizing enzymes, suggesting that the steroid sensor mechanism is active in the appropriate tissue. In addition, prominent expression is also found in the intestine. Although less is known about the role of this tissue in steroid or xenobiotic metabolism, it is certainly possible that the intestine plays a role in regulating the metabolism of dietary, and perhaps endogenous, steroids. Taken together, these data strongly support the existence of a class of low-affinity, broad-specificity nuclear hormone receptor(s), such as SXR, which function as intracellular "steroid sensor(s)".

The localization of apparent SXR-responsive elements in genes encoding steroid hydroxylases raises the question of whether products of steroid catabolism, such as reduced or hydroxylated corticosterone derivatives, could also activate SXR. FIG. 5 shows that both 5$\alpha$ and 5$\beta$ reduced forms of corticosterone are effective SXR activators whereas 5$\alpha$ is slightly active and 5$\beta$ is completely inactive on GR. While a few 5$\alpha$-reduced steroids remain active (e.g., dihydrotestosterone), virtually all 5$\beta$-reduced steroids are unable to activate classical steroid receptors (see Russell and Wilson in *Ann. Rev. Biochem.* 63:25 (1994)). Accordingly, the activation of SXR by 5$\beta$-reduced steroids reveals a previously unidentified role for these compounds in gene regulation.

6$\beta$-hydroxy corticosterone is virtually inactive on SXR and slightly active on GR (see FIG. 5) CYP3A genes, which contain SXR-activatable response elements, catalyze the hydroxylation of many steroids at the 6 position. Therefore, the inability of 6$\beta$-hydroxy-corticosterone to activate SXR suggests that 6-hydroxylation is a potential regulatory step in the SXR signaling pathway.

In accordance with the present invention, it has been discovered that induction of some xenobiotic-metabolizing enzymes by pharmacological levels of steroids is regulated by a member of the SXR class of broad-specificity, low-affinity, nuclear hormone receptors. One benefit of such a receptor-based system is that it induces the expression of xenobiotic metabolizing enzymes only at high activator levels, thus preventing interference with normal endocrine function. It also makes biological sense that the expression of enzymes with broad substrate specificity, such as cytochrome P450s, can be induced by a receptor responsive to a diverse group of activators, some of which can be substrates for the induced enzymes.

In support of the role for members of the SXR class of nuclear receptors proposed herein, it is demonstrated herein that SXR is activated by an extremely diverse group of steroids and their metabolites, including molecules that have high-affinity receptors such as progesterone, testosterone, estrogen and corticosterone as well as their reduced catabolites that are, for the most part, inactive on the high-affinity receptors. In addition to the natural steroids, SXR is activated by synthetic steroids including PCN and dexamethasone. These data provide a molecular explanation for the paradoxical induction of the CYP3A genes (a.k.a. P450$_{PCN}$)

by both glucocorticoid receptor agonists and antagonists since the cyp3A genes harbor a SXR-activatable response element in the promoter region that has been shown to be responsible for PCN and glucocorticoid induction (see Burger et al. supra and Gonzalez et al. supra). Whereas such a result is unexplainable by regulation of traditional, high-affinity steroid receptors, such behavior is consistent with the observed properties of the newly characterized steroid X receptor.

In accordance with another embodiment of the present invention, there are provided heterodimer complexes which consist of the above-described receptor polypeptide and RXR or other silent partner therefor.

In accordance with yet another embodiment of the present invention, there are provided isolated nucleic acids which encode the above-described receptor polypeptides. As used herein, the phrase "isolated nucleic acid" means a nucleic acid that is in a form that does not occur in nature. One means of isolating a nucleic acid encoding a polypeptide is to probe a mammalian genomic library with a natural or artificially designed DNA probe using methods well known in the art. DNA probes derived from the SXR gene are particularly useful for this purpose. DNA and cDNA molecules that encode SXR polypeptides can be used to obtain complementary genomic DNA, cDNA or RNA from human, mammalian (e.g., mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding SXR.

Exemplary DNAs include those which encode substantially the same amino acid sequence as shown in SEQ ID NO:2 (e.g., a contiguous nucleotide sequence which is substantially the same as nucleotides 493–1884 shown in SEQ ID NO:1). Presently preferred DNAs include those which encode the same amino acid sequence as shown in SEQ ID NO:2 (e.g., a contiguous nucleotide sequence which is the same as nucleotides 493–1884 shown in SEQ ID NO:1).

As used herein, nucleotide sequences which are substantially the same share at least about 90% identity, and amino acid sequences which are substantially the same typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention. As readily recognized by those of skill in the art, various ways have been devised to align sequences for comparison, e.g., the Blosum 62 scoring matrix, as described by Henikoff and Henikoff in *Proc. Natl. Acad. Sci.* USA 89:10915 (1992). Algorithms conveniently employed for this purpose are widely available (see, for example, Needleman and Wunsch in *J. Mol. Biol.* 48:443 (1970).

In accordance with still another embodiment of the present invention, there are provided nucleic acid constructs comprising the above-described nucleic acid, operatively linked to regulatory element(s) operative for transcription of said nucleic acid and expression of said polypeptide in an animal cell in culture. There are also provided cells containing such construct, optionally containing a reporter vector comprising:

(a) a promoter that is operable in said cell,
(b) a hormone response element, and
(c) DNA encoding a reporter protein,
   wherein said reporter protein-encoding DNA is operatively linked to said promoter for transcription of said DNA, and
   wherein said promoter is operatively linked to said hormone response element for activation thereof.

In accordance with a further embodiment of the present invention, there are provided methods of making invention receptor polypeptide(s), said methods comprising culturing cells containing an expression vector operable in said cells to express a DNA sequence encoding said polypeptide.

In accordance with a still further embodiment of the present invention, there are provided probes comprising labeled single-stranded nucleic acid, comprising at least 20 contiguous bases in length having substantially the same sequence as any 20 or more contiguous bases selected from bases 1–2068, inclusive, of the DNA illustrated in SEQ ID NO:1, or the complement thereof. An especially preferred probe of the invention comprises at least 20 contiguous bases in length having substantially the same sequence as any 20 or more contiguous bases selected from bases 493–1884, inclusive, of the DNA illustrated in SEQ ID NO:1, or the complement thereof.

Those of skill in the art recognize that probes as described herein can be labelled with a variety of labels, such as for example, radioactive labels, enzymatically active labels, fluorescent labels, and the like. A presently preferred means to label such probes is with $^{32}$P. Such probes are useful, for example, for the identification of receptor polypeptide(s) characterized by being responsive to the presence of steroid (s) to regulate the transcription of associated gene(s), said method comprising hybridizing test DNA with a probe as described herein under high stringency conditions (e.g., contacting probe and test DNA at 65° C. in 0.5M NaPO$_4$, pH 7.3, 7% sodium dodecyl sulfate (SDS) and 5% dextran sulfate for 12–24 hours; washing is then carried out at 60° C. in 0.1x SSC, 0.1% SDS for three thirty minute periods, utilizing fresh buffer at the beginning of each wash), and thereafter selecting those sequences which hybridize to said probe.

In another aspect of the invention, the above-described probes can be used to identify invention receptor polypeptide(s), or functional fragments thereof, said methods comprising hybridizing test DNA with a probe as described herein under high stringency conditions, and selecting those sequences which hybridize to said probe.

In yet another aspect of the invention, the above-described probes can be used to assess the tissue sensitivity of an individual to exposure to steroid and steroid-like compounds by determining SXR mRNA levels in a given tissue sample. It is expected that an individual having a high level of SXR mRNA (or protein) will be sensitive to the presence of significant levels of steroid and steroid-like compounds, such as are encountered in many foods, or as a result of overproduction and/or reduced ability to degrade steroids, as seen in such diseases as Cushing's syndrome, virilism and hirsutism in females, polycystic ovarian syndrome, and the like.

In accordance with yet another embodiment of the present invention, there are provided antibodies which specifically bind the above-described receptor polypeptides. Preferably, such antibodies will be monoclonal antibodies. Those of skill in the art can readily prepare such antibodies having access to the sequence information provided herein regarding invention receptors.

Thus, the above-described antibodies can be prepared employing standard techniques, as are well known to those of skill in the art, using the invention receptor proteins or portions thereof as antigens for antibody production. Both anti-peptide and anti-fusion protein antibodies can be used (see, for example, Bahouth et al. *Trends Pharmacol Sci.* 12:338–343 (1991); *Current Protocols in Molecular Biology* (Ausubel et al., eds.) John Wiley and Sons, New York (1989)). Factors to consider in selecting portions of the invention receptors for use as immunogen (as either a synthetic peptide or a recombinantly produced bacterial fusion protein) include antigenicity, uniqueness to the particular subtype, and the like.

The availability of such antibodies makes possible the application of the technique of immunohistochemistry to monitor the distribution and expression density of invention receptors. Such antibodies could also be employed for diagnostic and therapeutic applications.

In accordance with a further embodiment of the present invention, binding assays employing SXRs are provided, useful for rapidly screening a large number of compounds to determine which compounds (e.g., agonists and antagonists) are capable of binding to the receptors of the invention. Subsequently, more detailed assays can be carried out with initially identified compounds, to further determine whether such compounds act as agonists or antagonists of invention receptors.

The invention binding assays may also be employed to identify new SXR-like ligands. Test samples (e.g., biological fluids) may also be subjected to invention binding assays to detect the presence or absence of SXR or SXR ligands.

Another application of the binding assay of the invention is the assay of test samples (e.g., biological fluids) for the presence or absence of SXR. Thus, for example, tissue homogenates from a patient displaying symptoms thought to be related to over- or under-production of steroids can be assayed to determine if the observed symptoms are related to the presence of SXR.

The binding assays contemplated by the present invention can be carried out in a variety of ways, as can readily be identified by one of skill in the art. For example, competitive binding assays can be employed, as well as radioimmunoassays, ELISA, ERMA, and the like.

In accordance with yet another embodiment of the present invention, there is provided a method of testing a compound for its ability to regulate transcription-activating effects of invention receptor polypeptide(s), said method comprising assaying for the presence or absence of reporter protein upon contacting of cells containing said receptor polypeptide and reporter vector with said compound;
  wherein said reporter vector comprises:
    (a) a promoter that is operable in said cell,
    (b) a hormone response element, and
    (c) DNA encoding a reporter protein,
      wherein said reporter protein-encoding DNA is operatively linked to said promoter for transcription of said DNA, and
      wherein said promoter is operatively linked to said hormone response element for activation thereof.

Hormone response elements suitable for use in the above-described assay method comprise direct or inverted repeats of at least two half sites (each having the sequence RGBNNM, as defined herein). In each half site, RGBNNM:
  R is selected from A or G;
  B is selected from G, C, or T;
  each N is independently selected from A, T, C, or G; and
  M is selected from A or C;
    with the proviso that at least 4 nucleotides of said -RGBNNM- sequence are identical with the nucleotides at corresponding positions of the sequence AGTTCA.

Those of skill in the art recognize that the spacing between half sites can vary over a considerable range, typically falling in the range of about 0 up to 15 nucleotides. When the half sites are oriented as direct repeats, it is presently preferred that the half sites be separated by a spacer of 3, 4 or 5 nucleotides. Those of skill in the art recognize that any combination of 3, 4 or 5 nucleotides can be used as the spacer. Direct repeat response elements having a spacer of 4 nucleotides (e.g., SEQ ID NOS:6, 7 or 16) are presently preferred. When the half sites are oriented as inverted repeats, it is presently preferred that the half sites be separated by a spacer of 4, 5 or 6 nucleotides. Those of skill in the art recognize that any combination of 4, 5 or 6 nucleotides can be used as the spacer.

Optionally, the above-described method of testing can be carried out in the further presence of ligand for invention receptors, thereby allowing the identification of antagonists of invention receptors. Those of skill in the art can readily carry out antagonist screens using methods well known in the art. Typically, antagonist screens are carried out using a constant amount of agonist, and increasing amounts of a putative antagonist (i.e., a competitive assay). Alternatively, antagonists can be identified by rendering the receptor constitutively active (e.g., by adding a strong, constitutively-active activator to the receptor) and screening for compounds which shut down the resulting constitutively-active receptor.

In accordance with another aspect of the present invention, there are provided methods to identify compounds which are agonists of steroid X receptor (SXR), but which neither agonize nor antagonize other steroid receptors, said method comprising:
  detecting in a first assay system the presence or absence of reporter protein upon contacting of cells containing SXR and reporter vector with said compound;
  wherein said reporter vector comprises:
    (a) a promoter that is operable in said cell,
    (b) an SXR response element, and
    (c) DNA encoding a reporter protein,
      wherein said reporter protein-encoding DNA is operatively linked to said promoter for transcription of said DNA, and
      wherein said promoter is operatively linked to said SXR response element for activation thereof;
  detecting in a second assay system the presence or absence of reporter protein upon contacting of cells containing a steroid hormone receptor other than SXR and reporter vector with said compound;
  wherein said reporter vector comprises:
    (a) a promoter that is operable in said cell,
    (b) a response element for said receptor other than SXR, and
    (c) DNA encoding a reporter protein,
      wherein said reporter protein-encoding DNA is operatively linked to said promoter for transcription of said DNA, and
      wherein said promoter is operatively linked to said response element for said receptor other than SXR for activation thereof; and
  identifying those compounds which induce production of reporter in said first assay, but not in said second assay, as compounds which are agonists of steroid X receptor (SXR), but neither agonists nor antagonists of other steroid receptors.

Thus, it can readily be seen that invention methods can be used to identify a variety of therapeutically useful compounds. The compounds identified as described herein can be used for the treatment of a wide variety of indications, such as, for example:

a) Cushing's syndrome (hypercortisolism), which manifests as increased cortisol levels, leading to numerous problems including obesity, fatigue, hypertension, edema and osteoporosis;

b) virilism and hirsutism in females due to overproduction of testosterone;

c) androgen excess due to polycystic ovarian syndrome, which manifests as greatly increased circulating levels of dehydroepiandrosterone;

d) enzymatic defects which lead to accumulation of specific steroids, such as:
   1) 21-hydroxylase deficiency leading to increased synthesis of 17-hydroxy-progesterone and androgens;
   2) 11β-hydroxylase deficiency leading to deoxycortisol and deoxycorticosterone accumulation and attendant hypertension;
   3) 3β-hydroxysteroid dehydrogenase deficiency resulting in accumulation of pregnenolone and dehydroepiandrosterone, leading to sexual ambiguity in both sexes;
   4) 17-hydroxylase deficiency, which prevents cortisol synthesis but leads to accumulation of corticosterone and deoxycorticosterone, resulting in hypertension and aberrant development of secondary sexual characteristics in both sexes;

f) ameliorate the effect of substances in the diet and/or environment which act as endocrine disruptors, e.g., phytoestrogens which may be involved in breast, colorectal and prostate cancers (Adlercreutz and Mazur in *Ann. Med.* 29:95–120 (1997);

and the like. Compounds which are specific agonists for SXR without acting as either agonists or antagonists for other steroid receptors will find particular utility where other steroid compounds have been used for their catatoxic properties, while tolerating the negative effects of such therapeutic use (presumably caused by the undesirable activation of previously described steroid receptors, e.g., glucocorticoid receptor).

In accordance with a still further embodiment of the present invention, there are provided methods for modulating process(es) mediated by invention receptor polypeptides, said methods comprising conducting said process(es) in the presence of at least one agonist, antagonist or antibody raised against invention receptor.

In accordance with yet another embodiment of the present invention, there are provided methods for inducing the expression of steroid degradative enzymes, said method comprising activating SXR. Exemplary steroid degradative enzymes contemplated for expression herein include steroid hydroxylases, and the like.

The invention will now be described in greater detail by reference to the following non-limiting examples.

EXAMPLE 1 cDNA Isolation and Characterization

SXR was isolated in a screen to identify potential human homologs of the Xenopus benzoate 'X' receptor, BXR (also known as xONR-1) (see, for example, Smith et al., in *Nucl. Acids Res.* 22:66 (1994)). Thus, SXR was identified from a human genomic library (placenta, Clontech) hybridized with a full-length cDNA encoding the Xenopus orphan nuclear receptor BXR (see Blumberg, B., Kang, H., Bolado, J., Jr., Chen, H., Craig, A. G., Moreno, T. A., Umesono, K., Perlmann, T., De Robertis, E. M., and Evans, R. M., "BXR, an embryonic orphan nuclear receptor activated by a novel class of endogenous ligands," submitted to *Nature* for publication) under reduced stringency conditions (hybridization in 0.5M NaPO$_4$ pH 7.0, 7% SDS, 5% dextran sulfate at 65° C. overnight, washing three times twenty minutes in 2× SSC, 0.1% SDS at 37° C.).

Restriction mapping and Southern analysis showed that three exons were contained within the 9 kb EcoRI hybridizing fragment. This fragment was used to probe a human multiple tissue Northern blot (Clontech) at high stringency (hybridization as above, washing twice for 20 minutes in 0.1× SSC, 0.1% SDS at 50° C.) and hybridization was detected in liver.

A human liver cDNA library (Stratagene) was subsequently screened using the same conditions and four independent clones identified. Each of these was sequenced on both strands within the protein coding region. DNA sequences were compiled and aligned using the programs of Staden (*Nucl. Acids Res.* 14:217 (1986)) and the University of Wisconsin Genetics Computer Group (*Nucl. Acids Res.* 12:387 (1984)). Database searching was performed using the BLAST network server at the National Center for Biotechnology Information (see Altschul et al., in *J. Mol. Biol.* 215:403 (1990)).

The cDNA encodes a predicted protein of 464 amino acids (see SEQ ID NO:2) which is most closely, although distantly, related to BXR (73% amino acid identity in the DNA-binding domain (DBD), 52% in the ligand binding domain (LBD)), the vitamin D3 receptor and the orphan receptor CAR (see Baes et al., in *Mol. Cell. Biol.* 14:1544 (1994); see FIG. 1). Besides these receptors, SXR shows no more similarity to other nuclear receptors than the different receptor subfamilies do to each other (see FIG. 1). Since true homologs among nuclear receptors typically share considerable similarity, especially in the DBD, SXR is clearly an example of a novel class of receptors within the nuclear receptor superfamily.

A genomic clone encoding SXR has now been isolated, allowing the genomic site of SXR to be identified at 3q13.3.

EXAMPLE 2

Ability of SXR to Heterodimerize with RXR

Electrophoretic mobility shift assays were employed to determine the ability of SXR to heterodimerize with RXR and to analyze the selectivity and specificity of SXR DNA binding. DNA-binding analysis was performed as described by Perlmann et al (in *Genes Dev.* 7:1411 (1993)) using in vitro transcribed, translated proteins. The βDR-series oligonucleotides employed have been described previously (see Perlman et al., supra).

Direct repeat 0–15 (DR-0 up to DR-15) oligonucleotides employed herein had the following sequences:

DR-0: catagtc AGGTCA AGGTCA gatcaac (SEQ ID NO:12);

DR-1: catagtc AGGTCA t AGGTCA gatcaac (SEQ ID NO:13);

DR-2: catagtc AGGTCA at AGGTCA gatcaac (SEQ ID NO:14);

DR-3: catagtc AGGTCA tat AGGTCA gatcaac (SEQ ID NO:15);

DR-4: catagtc AGGTCA tata AGGTCA gatcaac (SEQ ID NO:16);

DR-5: catagtc AGGTCA tatat AGGTCA gatcaac (SEQ ID NO:17);

DR-6: catagtc AGGTCA tatata AGGTCA agatcaac (SEQ ID NO:18);

DR-7: catagtc AGGTCA tatatat AGGTCA gatcaac (SEQ ID NO:19);

DR-10: catagtc AGGTCA tatatatata AGGTCA gatcaac (SEQ ID NO:20);

DR-15: catagtc AGGTCA tagtagtagtagtag AGGTCA gatcaac (SEQ ID NO:21).

EXAMPLE 3

Cell Culture and Transfection Studies

To determine whether the activity of SXR was ligand-dependent, mixtures of natural and synthetic compounds were tested for their ability to activate SXR in transfection-based assays. Thus, the protein coding region of SXR was PCR amplified and subcloned into NcoI and BamH1 sites of the vector pCDG1 (see Blumberg et al., supra). During this process the putative initiator Leu was converted to Met with a Kozak consensus sequence CCATGG.

GAL4-SXR was constructed by cloning amino acid residues 134–446 of SXR into pCMX-GAL4 (see Perlman et al. supra). CV-1 cells were maintained in DMEM containing 10% resin-charcoal stripped calf bovine serum. Liposome-mediated transient transfections were performed using DOTAP reagent (Boehringer Manheim) at a concentration of 5 µg/ml in DMEM containing 10% resin charcoal stripped fetal bovine serum in 96-well format using a Beckman Biomek 1000 laboratory workstation as previously described by Blumberg et al., in *Proc. Natl. Acad. Sci. (USA)* 93:4873 (1996)).

Ligands were added the next day in DMEM containing 10% delipidated FBS. After 18–24 hours incubation, the cells were lysed and luciferase reporter gene assays and β-galactosidase transfection control assays performed as previously described by Blumberg et al. (1996), supra. Reporter gene expression was normalized to the β-galactosidase transfection control and expressed as relative light units per O.D. per minute of β-galactosidase activity or fold induction over solvent control. Each data point (see FIG. 2) represents the average of triplicate experiments ± standard error and was replicated in independent experiments.

While the invention has been described in detail with reference to certain preferred embodiments thereof, it will be understood that modifications and variations are within the spirit and scope of that which is described and claimed.

---

That which is claimed is:

1. A purified polynucleotide encoding a receptor polypeptide, wherein said polypeptide is a member of the steroid/thyroid hormone superfamily and is further characterized by:
   forming a heterodimer with retinoid X receptor (RXR), wherein said heterodimer binds to a direct or inverted repeat response element comprising at least two half sites RGBNNM separated by a spacer of 0 up to 15 nucleotides
   wherein;
   R is selected from A or G;
   B is selected from G, C, or T;
   each N is independently selected from A, T, C, or G; and
   M is selected from A or C;
   with the proviso that at least 4 nucleotides of said -RGBNNM- sequenceare identical with the nucleotides at corresponding positions of the sequence AGTTCA,
   activating transcription of a gene under the control of a cytochrome P450 response element in response to a wide variety of natural and synthetic steroid hormones, at least including compounds that induce catabolic enzymes, steroid receptor agonists and antagonists, and bioactive dietary compounds, and
   being detectably expressed in the liver and the intestine.

2. The purified polynucleotide according to claim 1 wherein said polynucleotide comprises a nucleotide sequence encoding a DNA binding domain having the same amino acid sequence as residues 71—137 of SEQ ID NO:2, or a conservative variation thereof.

3. An isolated nucleic acid construct comprising:
   (a) the polynucleotide of claim 2 operatively linked to
   (b) regulatory element(s) operative for transcription of said polynucleotide and expression of said polypeptide in an animal cell in culture.

4. The purified polynucleotide according to claim 1 wherein said polynucleotide comprises a nucleotide sequence encoding a ligand band binding domain having the same amino acid sequence as residues 267—464 of SEQ ID NO:2, or a conservative variation thereof.

5. An isolated nucleic acid construct comprising:
(a) the polynucleotide of claim 4 operatively linked to
(b) regulatory element(s) operative for transcription of said polynucleotide and expression of said polypeptide in an animal cell in culture.

6. The purified polynucleotide according to claim 1 wherein said polynucleotide encodes the amino acid sequence shown in SEQ ID NO:2, or conservative variations thereof.

7. An isolated nucleic acid construct comprising:
(a) the polynucleotide of claim 6 operatively linked to
(b) regulatory element(s) operative for transcription of said polynucleotide and expression of said polypeptide in an animal cell in culture.

8. The purified polynucleotide according to claim 1 wherein said polynucleotide encodes the amino acid sequence shown in SEQ ID NO:2.

9. An isolated nucleic acid construct comprising:
(a) the polynucleotide of claim 8 operatively linked to
(b) regulatory element(s) operative for transcription of said polynucleotide and expression of said polypeptide in an animal cell in culture.

10. The purified polynucleotide according to claim 1 wherein said polynucleotide comprises substantially the same nucleotide sequence shown in SEQ ID NO:1.

11. An isolated nucleic acid construct comprising:
(a) the polynucleotide of claim 10 operatively linked to
(b) regulatory element(s) operative for transcription of said polynucleotide and expression of said polypeptide in an animal cell in culture.

12. The purified polynucleotide according to claim 1 wherein said polynucleotide comprises the nucleotide sequence shown in SEQ ID NO:1.

13. The purified polynucleotide according to claim 1 comprising a segment of a contiguous nucleotide sequence having at least 90% sequence identity with nucleotides 493—1884 of SEQ ID NO:1.

14. An isolated nucleic acid construct comprising:
(a) the polynucleotide of claim 13 operatively linked to
(b) regulatory element(s) operative for transcription of said polynucleotide and expression of said polypeptide in an animal cell in culture.

15. The purified polynucleotide according to claim 1 comprising a segment of a contiguous nucleotide sequence having the same nucleotide sequence as nucleotides 493—1884 of SEQ ID NO:1.

16. The purified polynucleotide according to claim 1 wherein said polypeptide is further characterized by having a DNA binding domain of about 67 amino acids with 9 Cys residues, wherein said DNA binding domain has about 73% amino acid identity with the DNA binding domain of the Xenopus benzoate X receptor.

17. The purified polynucleotide according to claim 1 wherein said polypeptide is further characterized by having a ligand binding domain of about 198 amino acids, wherein said ligand binding domain has about 52% amino acid identity with the ligand binding domain of the Xenopus benzoate X receptor.

18. An isolated nucleic acid construct comprising:
(a) the polynucleotide of claim 1 operatively linked to
(b) regulatory element(s) operative for transcription of said polynucleotide and expression of said polypeptide in an animal cell in culture.

19. A purified polynucleotide selected from the group consisting of:
(a) polynucleotides having substantially the same sequence as SEQ ID NO:1 or SEQ ID NO:1 wherein T can also be U; and
(b) polynucleotides having at least 20 contiguous bases that hybridize under stringent conditions to the complement of SEQ ID NO:1;
wherein said polynucleotide encodes a receptor polypeptide, and wherein said polypeptide is a member of the steroid/thyroid hormone superfamily and is further characterized by:
forming a heterodimer with retinoid X receptor (RXR), wherein said heterodimer binds to a direct or inverted repeat response element comprising at least two half sites RGBNNM separated by a spacer of 0 up to 15 nucleotides,
wherein:
R is selected from A or G;
B is selected from G, C or T;
each N is independently selected from A, T, C or G; and
M is selected from A or C;
with the proviso that at least 4 nucleotides of said -RGBNNM- sequence are identical with the nucleotides at corresponding positions of the sequence AGTTCA,
activating transcription of a gene under control of a cytochrome P450 response element in response to a wide variety of natural and synthetic steroid hormones, at least including compounds that induce catabolic enzymes, steroid receptor agonists and antagonists, and bioactive dietary compounds, and
being detectably expressed in the liver and the intestine.

20. An isolated nucleic acid construct comprising:
(a) the polynucleotide of claim 19 operatively linked to
(b) regulatory element(s) operative for transcription of said polynucleotide and expression of said polypeptide in an animal cell in culture.

21. A purified polynucleotide encoding a receptor polypeptide having substantially the same amino acid sequence as set forth in SEQ ID NO:2, or conservative variations thereof, wherein said polypeptide is a member of the steroid/thyroid hormone superfamily and is further characterized by:
forming a heterodimer with retinoid X receptor (RXR), wherein said heterodimer binds to a direct or inverted repeat response element comprising at least two half sites RGBNNM separated by a spacer of 0 up to 15 nucleotides,
wherein:
R is selected from A or G;
B is selected from G, C or T;
each N is independently selected from A, T, C or G; and
M is selected from A or C;
with the proviso that at least 4 nucleotides of said -RGBNNM- sequence are identical with the nucleotides at corresponding positions of the sequence AGTTCA,
activating transcription of a gene under control of a cytochrome P450 response element in response to a wide variety of natural and synthetic steroid hormones, at least including compounds that induce catabolic enzymes, steroid receptor agonists and antagonists, and bioactive dietary compounds, and
being detectably expressed in the liver and the intestine.

22. An isolated nucleic acid construct comprising:
(a) the polynucleotide of claim 21 operatively linked to
(b) regulatory element(s) operative for transcription of said polynucleotide and expression of said polypeptide in an animal cell in culture.

23. A purified polynucleotide comprising the sequence set forth in SEQ ID NO:1.

24. A purified polynucleotide encoding the amino acid sequence set forth in SEQ ID NO:2.

25. An isolated polynucleotide encoding a hormone steroid X receptor (SXR),
wherein said receptor comprises a ligand binding domain and a DNA binding domain;
wherein said ligand binding domain is encoded by a first polynucleotide sequence which hybridizes under stringent conditions to the complement of nucleotides 1291—1884 of SEQ ID NO:i;
wherein said ligand binding domain binds to a wide variety of natural and synthetic steroid hormones, at least including compounds that induce catabolic enzymes, steroid receptor agonists and antagonists, and bioactive dietary compounds; and
wherein said DNA binding domain is encoded by a second polynucleotide sequence which hybridizes under stringent conditions to the complement of nucleotides 703—903 of SEQ ID NO:1.

26. The isolated polynucleotide according to claim 25, wherein said polynucleotide has at least 90% nucleic acid identity with respect to the coding sequence of SEQ ID NO:1.

27. The isolated polynucleotide according to claim 25, wherein said polynucleotide encodes a polypeptide which has at least 95% amino acid identity with respect to SEQ ID NO:2.

28. A recombinant polynucleotide comprising a nucleic acid segment encoding a fusion protein, wherein said fusion protein comprises:
a DNA binding domain ; and
a ligand binding domain, wherein said ligand binding domain is encoded by a polynucleotide sequence which hybridizes under stringent conditions to the complement of nucleotides 1291—1884 of SEQ ID NO:1; and
wherein said fusion protein activates transcription of a gene under the control of a response element which recognizes said DNA binding domain in response to a wide variety of natural and synthetic steroid hormones, at least including compounds that induce catabolic enzymes, steroid receptor agonists and antagonists, and bioactive dietary compounds.

29. An isolated polynucleotide encoding a ligand binding domain of a human steroid X receptor (SXR),
wherein said ligand binding domain binds to a wide variety of natural and synthetic steroid hormones, at least including compounds that induce catabolic enzymes, steroid receptor agonists and antagonists, and bioactive dietary compounds, and
wherein said polynucleotide sequence encoding said ligand binding domain hybridizes under stringent conditions to the complement of nucleotides 1291—1884 of SEQ ID NO:1.

30. The isolated polynucleotide according to claim 29 wherein said ligand binding comprises amino acid residues 267—464 of SEQ ID NO:2; or conservative variations thereof.

31. The isolated polynucleotide according to claim 29, wherein said ligand binding domain is encoded by nucleotides 1291—1884 of SEQ ID NO:1.

* * * * *